United States Patent [19]

Wu et al.

[11] 4,203,926

[45] May 20, 1980

[54] HYDROXIDATION OF GASEOUS OLEFINS WITH ETHYLBENZENE HYDROPEROXIDE IN A HETEROGENEOUS LIQUID SYSTEM

[75] Inventors: Ching-Yong Wu, O'Hara Township, Allegheny County; Thaddeus P. Kobylinski, Gibsonia, both of Pa.

[73] Assignee: Gulf Research and Development Company, Pittsburgh, Pa.

[21] Appl. No.: 970,103

[22] Filed: Dec. 18, 1978

[51] Int. Cl.$^2$ .................... C07C 27/16; C07C 29/02; C07C 31/16; C07C 49/78
[52] U.S. Cl. .................................. 568/319; 568/815; 568/860
[58] Field of Search .................. 568/860, 814, 815; 260/592

[56] References Cited

U.S. PATENT DOCUMENTS

| | | | |
|---|---|---|---|
| 3,488,394 | 1/1970 | Cummins | 568/860 |
| 3,665,047 | 5/1972 | Gislon et al. | 260/669 QZ |
| 3,860,662 | 1/1975 | Kollar | 568/815 |

FOREIGN PATENT DOCUMENTS 950669  2/1964  United Kingdom .................... 568/860

*Primary Examiner*—Joseph E. Evans

[57] ABSTRACT

Ethylbenzene hydroperoxide and ethylene or propylene are converted to acetophenone, 1-phenylethanol and the corresponding glycol at high selectivity in a process in which ethylbenzene hydroperoxide is reacted with the olefin in a two-phase liquid, organic-aqueous reaction system in the presence of osmium tetroxide and cesium, rubidium or potassium hydroxide.

13 Claims, No Drawings

HYDROXIDATION OF GASEOUS OLEFINS WITH ETHYLBENZENE HYDROPEROXIDE IN A HETEROGENEOUS LIQUID SYSTEM

SUMMARY OF THE INVENTION

This invention relates to a procedure for reacting ethylene or propylene with ethylbenzene hydroperoxide to produce the corresponding glycol, acetophenone and 1-phenylethanol at high selectivities.

We have discovered a process by which ethylbenzene hydroperoxide can be converted to acetophenone and 1-phenylethanol and ethylene and propylene can be converted to the corresponding glycol at excellent overall selectivities. In our procedure a reactor containing a two-phase liquid system comprising ethylbenzene hydroperoxide, ethylbenzene, an organic polar solvent, an aqueous solution of cesium hydroxide, rubidium hydroxide or potassium hydroxide and osmium tetroxide is pressured with ethylene or propylene. The product mixture contains ethylene or propylene glycol, 1-phenylethanol, and acetophenone. No measurable amounts of undesired oxidation by-products are found in the product mixture.

DESCRIPTION OF THE INVENTION

Ethylene glycol is currently produced commercially in a multistage process from ethylene at an overall selectivity of about 50 to 65 percent. In the first step ethylene is oxidized to ethylene oxide at elevated temperature and pressure using oxygen and a silver-containing catalyst. The reaction requires very careful control of operating conditions to obtain a selectivity as high as 70 percent. Generally, at least about one-third of the ethylene is lost as carbon dioxide. The ethylene oxide is then hydrated either catalytically using a dilute aqueous solution of a strong acid or at high temperatures and pressures, with some diethylene and triethylene glycols being formed as by-products. Other methods for producing ethylene glycol have not been commercially attractive.

Propylene glycol is currently produced commercially by several multistage processes from propylene. In these processes propylene is converted to propylene oxide. The propylene oxide is then hydrated either catalytically using a dilute aqueous solution of a strong acid or at high temperatures and pressures, with some dipropylene and tripropylene glycols being formed as by-products. No method for the direct production of propylene glycol has been commercially attractive.

U.S. Pat. No. 4,049,724 describes the direct preparation of propylene glycol from propylene in a homogeneous aqueous system using osmium tetroxide and specifying water-soluble hydroperoxides such as tert-butyl hydroperoxide while a critical pH is maintained with a suitable combination of alkali metal buffering compounds. Ethylbenzene hydroperoxide, which is not water soluble, is not specified in the patent. When the reaction described in this patent was attempted using ethylbenzene hydroperoxide and a stoichiometric excess of propylene, a selectivity to propylene glycol of only two percent resulted.

We have surprisingly discovered that ethylbenzene hydroperoxide and ethylene or propylene can readily react in a two-phase, organic-aqueous system containing ethylbenzene, an organic polar solvent, an aqueous hydroxide of cesium, rubidium or potassium and osmium tetroxide to form ethylene or propylene glycol at a selectivity based on the olefin of greater than 95 percent and greater than 80 percent based on the ethylbenzene hydroperoxide. Furthermore, the reaction produces acetophenone and 1-phenylethanol in substantially 100 percent selectivity, with no measurable amounts of oxidation by-products being found in the product mixture. And most surprisingly, the presence of aqueous cesium or rubidium hydroxide is effective in producing the desired reaction to the glycol, while the aqueous hydroxides of sodium and lithium are essentially ineffective, with potassium hydroxide being only moderately effective.

Ethylbenzene hydroperoxide is prepared as a solution in ethylbenzene by the air oxidation of ethylbenzene at a temperature between about 120° C. and about 150° C. A yield of up to about 25 percent ethylbenzene hydroperoxide can be obtained at a selectivity of about 80 to 95 percent depending on the reaction conditions. The primary by-products are acetophenone and 1-phenylethanol which are recovered together with the glycol after the hydroxidation reaction.

In the present invention the reaction of ethylbenzene hydroperoxide with ethylene or propylene is carried out in a heterogeneous, two-phase liquid reaction. It has previously been recognized that when the relatively unstable ethylbenzene hydroperoxide is utilized in a heterogeneous, two-phase reaction, a substantial portion of the ethylbenzene hydroperoxide decomposes in the nonreacting phase. Therefore, we had determined, as set out in patent application Ser. No. 948,243, filed Oct. 3, 1978, that a homogeneous reaction system is essential for high selectivity. Since ethylbenzene hydroperoxide is not significantly soluble in water, we had concluded that a nonaqueous reaction medium must be used to obtain a homogeneous reaction system. Notwithstanding this prior knowledge we have now surprisingly discovered by the present invention that a homogeneous reaction system is not required for the reaction of ethylbenzene hydroperoxide.

If the reaction of ethylene or propylene with ethylbenzene hydroperoxide is carried out under anhydrous conditions, 1-phenylethanol, acetophenone and the corresponding glycol are produced in equimolar amounts by the reaction of two mols of the hydroperoxide with each mol of the olefin. If water, which is slightly soluble in the organic phase, is present in the reaction vessel, it will enter into the reaction such that equimolar amounts of the hydroperoxide, olefin and water react to form equimolar amounts of 1-phenylethanol and the glycol. Since in actual practice both reactions take place when water is present, the product is a mixture of 1-phenylethanol, acetophenone, and the glycol with the 1-phenylethanol and glycol predominating on a molar basis.

The organic polar solvent can be an aliphatic or aromatic alcohol having from one to about ten carbon atoms, an aliphatic or aromatic ketone having from three to about ten carbon atoms, an aliphatic or alicyclic ether having from two to about ten carbon atoms, a glycol having from two to about ten carbon atoms, a N,N-dialkyl amide having from three to about ten carbon atoms, an aliphatic or aromatic sulfoxide having from two to about fourteen carbon atoms, an aliphatic or aromatic sulfone having from two to about fourteen carbon atoms, and the like. Examples of suitable polar solvents include methanol, ethanol, propanol, butanol, hexanol, decanol, benzyl alcohol, acetone, methylethyl, ketone, methylbutyl ketone, acetophenone, ethylene glycol, propylene glycol, diethylene glycol, tetraethylene glycol, dimethyl formamide, diethyl formamide, dimethyl acetamide, dimethyl sulfoxide, diethyl sulfoxide, di-n-butyl sulfoxide, diphenyl sulfoxide, dibenzyl sulfoxide, dimethyl sulfone, diethyl sulfone, tetramethylene sulfone, diphenyl sulfone, acetonitrile, pyridine, dioxane, tetrahydrofuran, tetrahydropyran, dioxolane, and the like. The amount of polar solvent can be between about 30 and about 98 weight percent of the reaction mixture, but will preferably comprise between about 50 and 80 percent of the reaction mixture. The preferred organic polar solvents are those which resist oxidation in the reaction system.

The amount of ethylbenzene hydroperoxide used in the reaction is not critical but will generally be from about one percent to about 20 weight percent of the total reaction mixture preferably from about five percent to about 20 percent of the reaction mixture. The amount of ethylbenzene in the reaction system can vary between about 2.5 percent and about 50 weight percent but at preferred conditions of operation it will comprise between about ten and about 30 weight percent of the total reaction mixture.

Since ethylene and propylene are gases, they are incorporated into the reaction system by pressuring the reactor with the olefin. The pressure is not critical, rather it determines the amount of the olefin that is present in the reaction liquid and therefore affects the rate of reaction. We find that a pressure between about 25 and about 1,500 psig. is useful for ethylene, and a pressure of between about 5 and about 150 psig. is useful for propylene. However, we prefer to operate within a pressure range of between about 50 and about 150 psig. for ethylene and a pressure between about 10 and about 50 psig. for propylene as providing a suitable reaction rate without requiring high pressure equipment. The reaction is preferably carried out with a stoichiometric excess of the olefin to substantially completely react all of the ethylbenzene hydroperoxide in the reaction mixture, and more preferably at least about a 25 percent stoichiometric excess of the olefin.

The aqueous solution of the alkali metal hydroxide is critical to the success of this heterogeneous liquid reaction. We have found that cesium hydroxide and rubidium hydroxide are highly useful in our process with potassium hydroxide being only moderately effective while sodium hydroxide and lithium hydroxide are practically ineffective. Since, as we have determined, the yield of the glycol decreases as the molecular weight of the alkali metal hydroxide decreases, cesium hydroxide is preferred for the present process.

The cesium, rubidium or potassium hydroxide, or a mixture of these hydroxides, is introduced into the reaction zone as an aqueous solution. The amount of the hydroxide in the two-phase reaction mixture is not critical. As little as 0.1 weight percent of the alkali metal hydroxide based on the total reaction mixture is suitable, however, we prefer at least about 0.2 weight percent of the hydroxide. As much as about ten weight percent of the alkali metal hydroxide based on the total reaction mixture can be used, but we prefer that a maximum amount of about five weight percent of the hydroxide be used. The amount of water present in the two-phase reaction mixture can be between about one and about 40 weight percent based on the total reaction mixture, and preferably can be between about two and about 20 weight percent, provided that sufficient water is used to dissolve the alkali metal hydroxide.

The catalyst, osmium tetroxide, is used in catalytic quantities. We find that from 0.01 to ten mmols of the catalyst per 100 ml. of the total reaction mixture is suitable, however, we prefer to carry out the reaction using from about 0.03 to about 0.1 mmol of catalyst per 100 ml. of the reaction mixture. The amount of catalyst can also be related to the amount of osmium metal that is used. Thus, about 50 to about 1,000 ppm. osmium can be used based on the total liquid contents of the reaction vessel, preferably about 100 to about 500 ppm. osmium. It is preferred that the osmium catalyst be added after the reactor has been pressured with the olefin since osmium catalyzes the decomposition of the hydroperoxide in the olefin's absence.

Osmium tetroxide is readily soluble in aqueous solutions of a strong base, such as alkali metal hydroxide, with which it rapidly reacts to form the perosmate, an ionic complex. Since osmium tetroxide is also soluble in many organic polar solvents, it can be dissolved in a suitable organic polar solvent for addition to the reactor where it quickly reacts with the alkali metal hydroxide forming the ionic perosmate in the aqueous solution. There must be at least a 2:1 gram atom ratio of the alkali metal to osmium metal and preferably a gram atom ratio of at least about 10:1 to provide for the perosmate complex.

We believe that in the two-phase liquid reaction mixture of our invention the osmium tetroxide functions as an oxidant in the form of the perosmate and that the osmate reduction product is oxidized back to the perosmate oxidizer by the ethylbenzene hydroperoxide. For this reason an alkali metal osmate or perosmate, preferably the cesium, rubidium or potassium complex that corresponds to the alkali metal hydroxide that is in the reactor, can be added directly to the reactor instead of osmium tetroxide. Therefore, in this specification including the claims reference to osmium tetroxide is intended to include within its scope the alkali metal osmates and perosmates.

The hydroxidation reaction is carried out at a moderate temperature. At higher temperatures the reaction rate increases substantially but this occurs at a significant reduction in selectivity to the glycol. At very low temperatures the selectivity to glycol is excellent but the reaction rate is slow. Within those constraints we find that a moderate reaction temperature is desirable including the range of about −10° C. to about 50° C., but we prefer to operate within the range of about 0° C. to about 25° C.

This hydroxidation reaction can be carried out as a batch reaction, or as a semi-continuous batch reaction. In the batch reaction all the necessary components are placed in a reaction vessel and the reaction is allowed to proceed for about one to about 24 hours for substantially complete reaction of the ethylbenzene hydroperoxide. The reaction can be carried out in a semi-continuous manner by metering the reaction components into an agitated tank reactor, or a series of tank reactors, pressured with the olefin and removing the reaction product mixture at an appropriate rate to maintain the reactor liquid level.

The reaction product, after removal of unreacted gaseous olefin, is a two-phase mixture. It includes ethylene or propylene glycol, 1-phenylethanol and acetophenone and also the polar solvent, ethylbenzene, the alkali metal hydroxide, an osmium compound and water.

Since the reaction is generally carried out under conditions, including a stoichiometric excess of olefin for complete reaction of the ethylbenzene hydroperoxide, there is no significant amount of hydroperoxide in the reaction product. If unreacted ethylbenzene hydroperoxide shows up in the reaction product, it is removed by the use of a suitable reducing agent in an extra processing step as a safety precaution to avoid possible hazards resulting from the undesired decomposition of the hydroperoxide during product work-up. Therefore, insuring the substantial absence of ethylbenzene hydroperoxide in the reaction product represents a safety precaution and avoids substantial processing costs.

The reaction product is characterized by the substantial absence of oxidation products of the olefin other than the glycol corresponding to the olefin. We believe that this substantial absence of undesired oxidation by-products is, at least in part, a result of the use of a stoichiometric excess of the olefin in the reaction zone. The volatile components are distilled out of the reaction mixture into various fractions. The osmium tetroxide or other osmium compounds remain in the still. Ethylene or propylene glycol is separated from the high boiling distillate leaving a mixture of the 1-phenylethanol and acetophenone for further processing. The mixture of 1-phenylethanol and acetophenone predominates in 1-phenylethanol generally in an amount between about 60 and 70 percent. This mixture can be converted to styrene by a suitable combination of hydrogenation and dehydration operations.

DESCRIPTION OF PREFERRED EMBODIMENTS

Examples 1-9

A series of reactions were carried out using different alkali metal hydroxides and varying concentrations of these hydroxides. The reactor, cooled to 0° C. in an ice-salt bath, was located in a steel safety box because of the olefin pressure that was used. The reactor was charged with 100 ml. of t.butanol, or in one experiment 100 ml. of acetone, and the aqueous solution of the alkali metal hydroxide was introduced. After the solution had cooled to 0° C., 61 ml. of 19.8 percent ethylbenzene hydroperoxide in ethylbenzene was added. Ethylene was pressured into the reactor to about 120 psi. followed by five ml. of 0.5 weight percent osmium tetroxide (0.1 mmol) in t.butanol which was pressured into the reactor in a stream of ethylene. Although all liquids added to the reactor were clear, two colored phases were observed in the reactor, a light yellow organic phase on top and a dark brown aqueous phase on the bottom.

The stirrer was started and the ethylene pressure was adjusted to 150 psi. This pressure and a temperature of 0° C. was maintained for six hours, at which time the reaction was near completion. In order to permit completion of the reaction, the reactor was permitted to stand at room temperature overnight. After evaporation of the solvent, the product was analyzed by gas-liquid chromatography. The yield of ethylene glycol based on the ethylbenzene hydroperoxide charged to the reactor is set out in the following table.

Table

| Example | Base | Conc., wt. % | ml. | Yield, wt. % |
|---|---|---|---|---|
| 1 | CsOH | 10 | 15 | 83.7 |
| 2 | CsOH | 10 | 7.5 | 67.0 |
| 3 | CsOH | 5 | 7.5 | 53.5 |

Table-continued

| Example | Base | Conc., wt. % | ml. | Yield, wt. % |
|---|---|---|---|---|
| 4 | CsOH | 20 | 7.5 | 52.6 |
| 5[a] | CsOH | 10 | 7.5 | 72.1 |
| 6 | RbOH | 10 | 7.5 | 60.6 |
| 7 | KOH | 10 | 7.5 | 41.7 |
| 8 | NaOH | 10 | 7.5 | 23.1 |
| 9 | LiOH | 10 | 7.5 | 8.2 |

[a] Used 100 ml. of acetone

Example 10

In this experiment the reaction of tert-butyl hydroperoxide and propylene in an aqueous, buffered system is reviewed.

A 300 ml. thick-walled glass reactor equipped with a stirring magnet was charged with 18.5 g. of water, 1.0 g. $Na_2CO_3$, 1.2 g. $NaHCO_3$ and 0.2 mmol of osmium tetroxide. A measured 26 g. portion of propylene and 15 cc. of 70 percent tert-butyl hydroperoxide (98 mmols) were charged into the reactor. The reaction mixture was stirred at ambient temperature (20°–25° C.) for two hours. The reaction temperature rose from 25° C. to 45° C. and then slowly dropped back to 25° C. The stirring was continued for an additional 30 minutes to insure complete reaction of the hydroperoxide. Analysis of the reaction product disclosed the production of 1.7 g. (22.4 mmols) of propylene glycol which was a selectivity of 23 percent based on the tert-butyl hydroperoxide.

Example 11

In this embodiment it is demonstrated that the procedure including an aqueous, buffered reaction system as described in Example 10 is not useful for the preparation of propylene glycol from ethylbenzene hydroperoxide and propylene.

The procedures and quantities of Example 3 were repeated except that 33 g. of propylene were used and the tert-butyl hydroperoxide was replaced with 71.5 g. of 19 percent ethylbenzene hydroperoxide (98 mmols). Analysis of the product disclosed that 0.17 g. of propylene glycol had been produced (2.24 mmols) which is a selectivity of 2.3 percent based on the ethylbenzene hydroperoxide.

It is to be understood that the above disclosure is by way of specific example and that numerous modifications and variations are available to those of ordinary skill in the art without departing from the true spirit and scope of the invention.

We claim:

1. A method of concurrently preparing a glycol, acetophenone and 1-phenylethanol which comprises contacting ethylbenzene hydroperoxide with ethylene or propylene at an elevated pressure in a heterogeneous, two-phase liquid reaction system comprising ethylbenzene, an organic polar solvent, a catalytic quantity of osmium tetroxide and an aqueous solution of cesium hydroxide, rubidium hydroxide or potassium hydroxide at a moderate temperature.

2. A method of concurrently preparing a glycol, acetophenone and 1-phenylethanol in accordance with claim 1 in which the temperature is between about −20° C. and about 50° C.

3. A method of concurrently preparing a glycol, acetophenone and 1-phenylethanol in accordance with claim 1 in which there is between about 2.5 and about 50 weight percent ethylbenzene.

4. A method of concurrently preparing a glycol, acetophenone and 1-phenylethanol in accordance with claim 1 in which there is between about 30 and about 98 weight percent of the organic polar solvent.

5. A method of concurrently preparing ethylene glycol, acetophenone and 1-phenylethanol in accordance with claim 1 in which the pressure of ethylene in the reaction zone is between about 25 and about 1,500 psig.

6. A method of concurrently preparing a glycol, acetophenone and 1-phenylethanol in accordance with claim 1 in which there is between about one to about 20 weight percent ethylbenzene hydroperoxide.

7. A method of concurrently preparing a glycol, acetophenone and 1-phenylethanol in accordance with claim 4 in which the polar solvent is selected from aliphatic alcohols, aliphatic ketones and aliphatic ethers having up to about six carbon atoms.

8. A method of concurrently preparing a glycol, acetophenone and 1-phenylethanol in accordance with claim 2 in which there is about 50 to about 1,000 ppm. osmium as the metal based on the total reaction mixture.

9. A method of concurrently preparing a glycol, acetophenone and 1-phenylethanol in accordance with claim 1 in which there is about 0.1 to about ten weight percent of the alkali metal hydroxide and about one to about 40 weight percent water.

10. A method of concurrently preparing propylene glycol, acetophenone and 1-phenylethanol in accordance with claim 1 in which the pressure of propylene is between about 5 and about 150 psig.

11. A method of concurrently preparing a glycol, acetophenone and 1-phenylethanol in accordance with claim 1 in which the alkali metal hydroxide is cesium hydroxide.

12. A method of concurrently preparing a glycol, acetophenone and 1-phenylethanol in accordance with claim 1 in which there is between about 0.1 and about ten weight percent of the alkali metal hydroxide and between about one and about forty weight percent water based on the total liquid reaction mixture.

13. A method of concurrently preparing ethylene glycol, acetophenone and 1-phenylethanol which comprises contacting ethylbenzene hydroperoxide with a stoichiometric excess of ethylene under a pressure of about 50 to about 150 psig. in a heterogeneous, two-phase liquid reaction system comprising about ten to about 30 weight percent ethylbenzene and about 50 to about 80 weight percent of an organic polar solvent based on the total reaction mixture, about 0.01 to about ten mmols of osmium tetroxide per 100 ml. of the reaction mixture, about 0.2 to about five weight percent of cesium hydroxide and about two to about 20 weight percent water at a temperature between about $-10°$ C. and about 50° C.

* * * * *

UNITED STATES PATENT OFFICE
CERTIFICATE OF CORRECTION

Patent No. 4,203,926                    Dated May 20, 1980

Inventor(s) Ching-Yong Wu and Thaddeus P. Kobylinski

It is certified that error appears in the above-identified patent and that said Letters Patent are hereby corrected as shown below:

Column 6, line 32, "embodiment" should read --experiment--.
Column 6, (claim 2) line 64, "-20° C." should read -- -10° C. --.

Signed and Sealed this

Twenty-sixth Day of August 1980

[SEAL]

Attest:

SIDNEY A. DIAMOND

Attesting Officer     Commissioner of Patents and Trademarks